(12) United States Patent
Izdebski et al.

(10) Patent No.: US 7,928,063 B2
(45) Date of Patent: Apr. 19, 2011

(54) ANALOGS OF HUMAN GROWTH HORMONE-RELEASING HORMONE, THEIR PREPARATION AND USE

(75) Inventors: Jan Izdebski, Warszawa (PL); Danuta Kunce, Warszawa (PL); Alicja Orlowska, Warszawa (PL); Ewa Witkowska, Warszawa (PL); Wieslaw Szelejewski, Warszawa (PL); Andrzej Kutner, Warszawa (PL); Krzysztof Bankowski, Warszawa (PL); Elzbieta Frackiewicz, Warszawa (PL)

(73) Assignees: Instytut Farmaceutyczny, Warszawa (PL); Zaklady Farmaceutyczne Polpharma, Starogard Gdanski (PL)

( * ) Notice: Subject to any disclaimer, the term of this patent is extended or adjusted under 35 U.S.C. 154(b) by 1419 days.

(21) Appl. No.: 10/494,218

(22) PCT Filed: Oct. 30, 2002

(86) PCT No.: PCT/PL02/00080
§ 371 (c)(1),
(2), (4) Date: Nov. 23, 2004

(87) PCT Pub. No.: WO03/037928
PCT Pub. Date: May 8, 2003

(65) Prior Publication Data
US 2006/0172927 A1 Aug. 3, 2006

(30) Foreign Application Priority Data
Oct. 31, 2001 (PL) .......................................... 350463

(51) Int. Cl.
*A61K 38/25* (2006.01)
(52) U.S. Cl. .................................................... 514/11.2
(58) Field of Classification Search .................. None
See application file for complete search history.

(56) References Cited

U.S. PATENT DOCUMENTS

| | | | | |
|---|---|---|---|---|
| 5,416,073 A * | 5/1995 | Coy et al. | .......................... | 514/12 |
| 5,792,747 A * | 8/1998 | Schally et al. | .................. | 514/12 |
| 6,380,358 B1 * | 4/2002 | Goodman et al. | ............. | 530/334 |

OTHER PUBLICATIONS

Schwegler ("Influence on the Trypsin Activity by the Side Chain of Arginine Homologues," Cellular and Molecular Life Sciences, 1976, 32, 1380-1).*
Frohman et al. ("Dipeptidylpeptidase IV and Trypsin-like Enzymatic Degradation of Human Growth Hormone-releasing Hormone in Plasma," J. Clin. Invest., 1989, 83, 1533-1540).*
Campbell et al. ("Rational Design, Synthesis, and Biological Evaluation of Novel Growth Hormone Releasing Factor Analogues," Biopolymers, 1995, 37, 67-88).*
Izdebski et al. "New Potent hGH-RH Analogues with Increased Resistance to Enzymatic Degradation." J. Peptide Science, 2002, 8, 289-296.*
Witkowska et al. ("Tryptic Hydrolysis of hGH-RH(1-29)-NH2 Analogues Containing Lys or Orn in Positions 12 and 21," J. Peptide Sci., 2001, 7, 166-172).*

* cited by examiner

*Primary Examiner* — Christina Bradley
(74) *Attorney, Agent, or Firm* — Ladas & Parry LLP

(57) ABSTRACT

Growth hormone-releasing hormone analogs having the amino acid sequence of the formula: Dat-Ala-Asp-Ala-Ile-Phe-Thr-Asn-Ser-Tyr$^{10}$-R$^{11}$-R$^{12}$-VAL-Leu-Ala-Gln-Leu-Ser-Ala-R$^{20}$-R$^{21}$-Leu-Leu-Gln-Asp-Ile-Nle-Asp-R$^{29}$-NH$_2$ (I), wherein R$^{11}$ is hArg, Gab or Gap; R$^{12}$ is hArg, Orn, Gab or Gap; R$^{20}$ is hArg, hArg, Gab or Gap; R$^{21}$ is hArg, Orn, Gab or Gap; R$^{29}$ is D-Arg, hArg, Gab or Gap; and their pharmaceutically acceptable salts. Said peptides are potent and selective stimulators of GH release and they are highly resistant to enzymatic degradation. Said peptides are prepared using the solid phase synthesis method, by introducing suitable derivatives of lysine, 2,4-diaminobutyric acid or 2,3-diaminopropionic acid at appropriate positions in the peptide chain attached to a polymeric support, deprotecting side-chain amino groups and reacting free amino groups with a guanidinating agent, removing all remaining t-butyloxycarbonyl protective groups, and cleaving the synthesized peptide from the support, followed by purification and optionally, converting the peptide into a pharmaceutically acceptable salt.

9 Claims, 2 Drawing Sheets

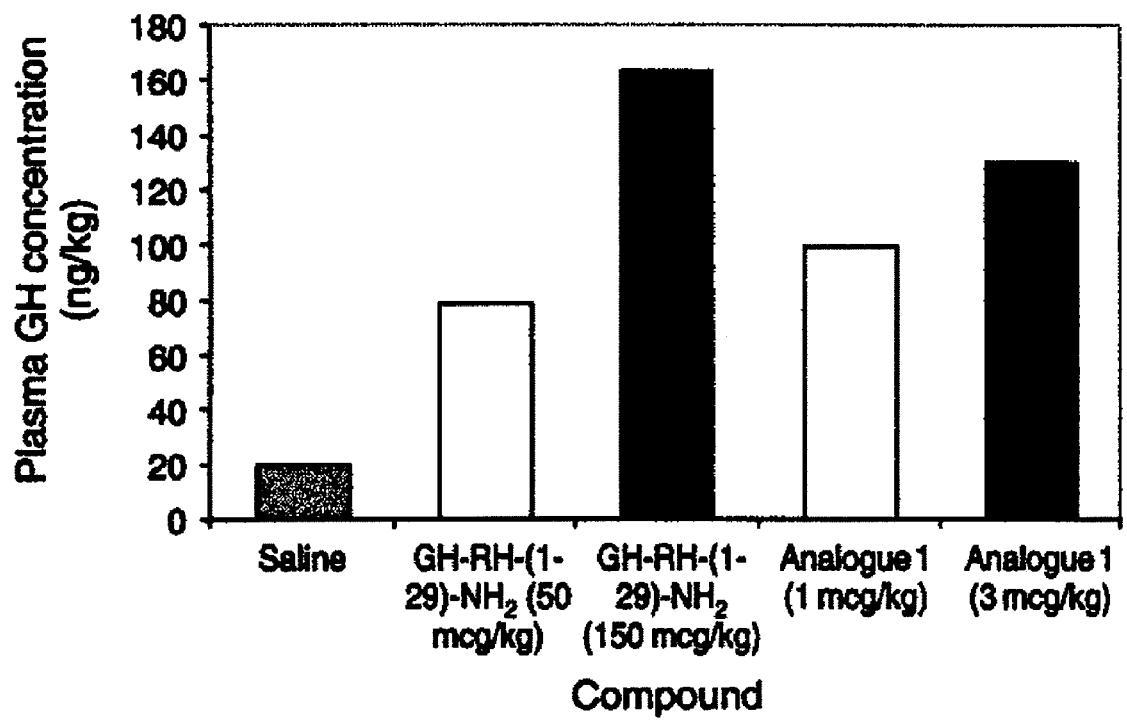
Figure 1  Plasma GH concentration 15 min after the injection of saline, hGH-RH-(1-29)-NH$_2$ and analogue 1.

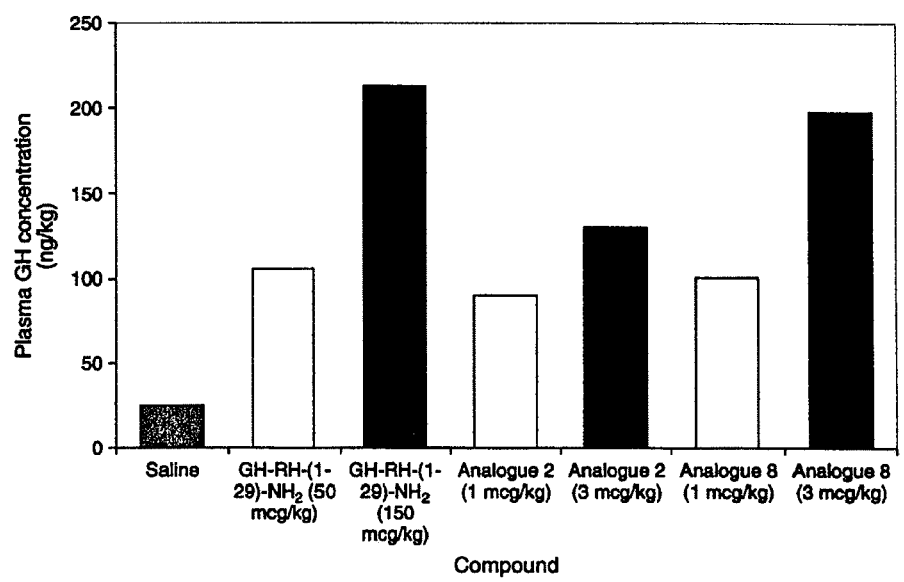
Figure 2 Plasma GH concentration 15 min after the injection of saline, hGH-RH-(1-29)-NH$_2$ and analogue 2 and analogue 8.

SEQUENCE LISTING

<160> NUMBER OF SEQ ID NOS: 9

<210> SEQ ID NO 1
<211> LENGTH: 29
<212> TYPE: PRT
<213> ORGANISM: Artificial sequence
<220> FEATURE:
<223> OTHER INFORMATION: Synthesized
<220> FEATURE:
<223> OTHER INFORMATION: Dat, desaminotyrosine, 3-(4'-hydroxyphenyl)

-continued

```
       propionic acid
<220> FEATURE:
<221> NAME/KEY: MISC_FEATURE
<222> LOCATION: (1)..(1)
<223> OTHER INFORMATION: Dat, desaminotyrosine, 3-(4'-hydroxyphenyl)
       propionic acid
<220> FEATURE:
<221> NAME/KEY: MISC_FEATURE
<222> LOCATION: (11)..(12)
<223> OTHER INFORMATION: hArg, homoarginine, 6-guanidino 2-amino caproic
       acid
<220> FEATURE:
<221> NAME/KEY: MISC_FEATURE
<222> LOCATION: (20)..(21)
<223> OTHER INFORMATION: hArg, homoarginine, 6-guanidino 2-amino caproic
       acid
<220> FEATURE:
<221> NAME/KEY: MISC_FEATURE
<222> LOCATION: (27)..(27)
<223> OTHER INFORMATION: Nle, norleucine
<220> FEATURE:
<221> NAME/KEY: MISC_FEATURE
<222> LOCATION: (29)..(29)
<223> OTHER INFORMATION: hArg-NH2, homoarginine amide, 6-guanidino
       2-amino caproic acid amide

<400> SEQUENCE: 1

Xaa Ala Asp Ala Ile Phe Thr Asn Ser Tyr Xaa Xaa Val Leu Ala Gln
1               5                   10                  15

Leu Ser Ala Xaa Xaa Leu Leu Gln Asp Ile Gln Asp Gln
            20                  25

<210> SEQ ID NO 2
<211> LENGTH: 29
<212> TYPE: PRT
<213> ORGANISM: Artificial sequence
<220> FEATURE:
<223> OTHER INFORMATION: Synthesized
<220> FEATURE:
<223> OTHER INFORMATION: Dat, desaminotyrosine, 3-(4'-hydroxyphenyl)
       propionic acid
<220> FEATURE:
<221> NAME/KEY: MISC_FEATURE
<222> LOCATION: (1)..(1)
<223> OTHER INFORMATION: Dat, desaminotyrosine, 3-(4'-hydroxyphenyl)
       propionic acid
<220> FEATURE:
<221> NAME/KEY: MISC_FEATURE
<222> LOCATION: (11)..(11)
<223> OTHER INFORMATION: hArg, homoarginine, 6-guanidino 2-amino caproic
       acid
<220> FEATURE:
<221> NAME/KEY: MISC_FEATURE
<222> LOCATION: (12)..(12)
<223> OTHER INFORMATION: Orn, ornithine
<220> FEATURE:
<221> NAME/KEY: MISC_FEATURE
<222> LOCATION: (20)..(20)
<223> OTHER INFORMATION: hArg, homoarginine, 6-guanidino 2-amino caproic
       acid
<220> FEATURE:
<221> NAME/KEY: MISC_FEATURE
<222> LOCATION: (21)..(21)
<223> OTHER INFORMATION: Orn, ornithine
<220> FEATURE:
<221> NAME/KEY: MISC_FEATURE
<222> LOCATION: (27)..(27)
<223> OTHER INFORMATION: Nle, norleucine
<220> FEATURE:
<221> NAME/KEY: MISC_FEATURE
<222> LOCATION: (29)..(29)
<223> OTHER INFORMATION: hArg-NH2, homoarginine amide, 6-guanidino
       2-amino caproic acid

<400> SEQUENCE: 2

Xaa Ala Asp Ala Ile Phe Thr Asn Ser Tyr Xaa Xaa Val Leu Ala Gln
```

```
                1               5                  10                  15
Leu Ser Ala Xaa Xaa Leu Leu Gln Asp Ile Xaa Asp Xaa
                20                  25

<210> SEQ ID NO 3
<211> LENGTH: 29
<212> TYPE: PRT
<213> ORGANISM: Artificial sequence
<220> FEATURE:
<223> OTHER INFORMATION: Synthesized
<220> FEATURE:
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (1)..(1)
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (11)..(12)
<223> OTHER INFORMATION: Gab, 4-guanidino 2-amino butyric acid
<220> FEATURE:
<221> NAME/KEY: MISC_FEATURE
<222> LOCATION: (20)..(21)
<223> OTHER INFORMATION: Gab, 4-guanidino 2-amino butyric acid
<220> FEATURE:
<221> NAME/KEY: MISC_FEATURE
<222> LOCATION: (27)..(27)
<223> OTHER INFORMATION: Nle, norleucine
<220> FEATURE:
<221> NAME/KEY: MISC_FEATURE
<222> LOCATION: (29)..(29)
<223> OTHER INFORMATION: Gab-NH2, 4-guanidino 2-amino butyric acid-amide

<400> SEQUENCE: 3

Xaa Ala Asp Ala Ile Phe Thr Asn Ser Tyr Xaa Xaa Val Leu Ala Gln
1               5                  10                  15

Leu Ser Ala Xaa Xaa Leu Leu Gln Asp Ile Xaa Asp Xaa
                20                  25

<210> SEQ ID NO 4
<211> LENGTH: 29
<212> TYPE: PRT
<213> ORGANISM: Artificial sequence
<220> FEATURE:
<223> OTHER INFORMATION: Synthesized
<220> FEATURE:
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (1)..(1)
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (11)..(11)
<223> OTHER INFORMATION: hArg, homoarginine, 6-guanidino 2-amino caproic
      acid
<220> FEATURE:
<221> NAME/KEY: MISC_FEATURE
<222> LOCATION: (12)..(12)
<223> OTHER INFORMATION: Gab, 4-guanidino 2-amino butyric acid
<220> FEATURE:
<221> NAME/KEY: MISC_FEATURE
<222> LOCATION: (20)..(21)
<223> OTHER INFORMATION: Gab, 4-guanidino 2-amino butyric acid
<220> FEATURE:
<221> NAME/KEY: MISC_FEATURE
<222> LOCATION: (27)..(27)
<223> OTHER INFORMATION: Nle, norleucine
<220> FEATURE:
<221> NAME/KEY: MISC_FEATURE
<222> LOCATION: (29)..(29)
```

```
<223> OTHER INFORMATION: Gab-NH2, 4-guanidino 2-amino butyric acid
      amine

<400> SEQUENCE: 4

Xaa Ala Asp Ala Ile Phe Thr Asn Ser Tyr Xaa Xaa Val Leu Ala Gln
1               5                   10                  15

Leu Ser Ala Xaa Xaa Leu Leu Gln Asp Ile Xaa Asp Xaa
            20                  25

<210> SEQ ID NO 5
<211> LENGTH: 29
<212> TYPE: PRT
<213> ORGANISM: Artificial sequence
<220> FEATURE:
<223> OTHER INFORMATION: Synthesized
<220> FEATURE:
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (1)..(1)
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (11)..(11)
<223> OTHER INFORMATION: Gab, 4-guandino 2-amino butyric acid
<220> FEATURE:
<221> NAME/KEY: MISC_FEATURE
<222> LOCATION: (12)..(12)
<223> OTHER INFORMATION: hArg, homoarginine, 6-guanidino 2-amino caproic
      acid
<220> FEATURE:
<221> NAME/KEY: MISC_FEATURE
<222> LOCATION: (20)..(21)
<223> OTHER INFORMATION: hArg, homoarginine, 6-guanidino 2-amino caproic
      acid
<220> FEATURE:
<221> NAME/KEY: MISC_FEATURE
<222> LOCATION: (27)..(27)
<223> OTHER INFORMATION: Nle, norleucine
<220> FEATURE:
<221> NAME/KEY: MISC_FEATURE
<222> LOCATION: (29)..(29)
<223> OTHER INFORMATION: D-Arg NH2, D-arginine amide

<400> SEQUENCE: 5

Xaa Ala Asp Ala Ile Phe Thr Asn Ser Tyr Xaa Xaa Val Leu Ala Gln
1               5                   10                  15

Leu Ser Ala Xaa Xaa Leu Leu Gln Asp Ile Xaa Asp Xaa
            20                  25

<210> SEQ ID NO 6
<211> LENGTH: 29
<212> TYPE: PRT
<213> ORGANISM: Artificial sequence
<220> FEATURE:
<223> OTHER INFORMATION: Synthesized
<220> FEATURE:
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (1)..(1)
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (11)..(11)
<223> OTHER INFORMATION: hArg, homoarginine, 6-guanidino 2-amino caproic
      acid
<220> FEATURE:
<221> NAME/KEY: MISC_FEATURE
<222> LOCATION: (12)..(12)
```

```
<223> OTHER INFORMATION: Gab, 4-guanidino 2-amino butyric acid
<220> FEATURE:
<221> NAME/KEY: MISC_FEATURE
<222> LOCATION: (20)..(21)
<223> OTHER INFORMATION: hArg, homoarginine, 6-guanidino 2-amino caproic
      acid
<220> FEATURE:
<221> NAME/KEY: MISC_FEATURE
<222> LOCATION: (27)..(27)
<223> OTHER INFORMATION: Nle, norleucine
<220> FEATURE:
<221> NAME/KEY: MISC_FEATURE
<222> LOCATION: (29)..(29)
<223> OTHER INFORMATION: D-Arge-NH2, D-arginine amide

<400> SEQUENCE: 6

Xaa Ala Asp Ala Ile Phe Thr Asn Ser Tyr Xaa Xaa Val Leu Ala Gln
1               5                   10                  15

Leu Ser Ala Xaa Xaa Leu Leu Gln Asp Ile Xaa Asp Xaa
            20                  25

<210> SEQ ID NO 7
<211> LENGTH: 29
<212> TYPE: PRT
<213> ORGANISM: Artificial sequence
<220> FEATURE:
<223> OTHER INFORMATION: Synthesized
<220> FEATURE:
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (1)..(1)
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (11)..(12)
<223> OTHER INFORMATION: Gap, 3-guanidino 2-amino propionic acid
<220> FEATURE:
<221> NAME/KEY: MISC_FEATURE
<222> LOCATION: (20)..(21)
<223> OTHER INFORMATION: Gap, 3-guanidino 2-amino propionic acid
<220> FEATURE:
<221> NAME/KEY: MISC_FEATURE
<222> LOCATION: (27)..(27)
<223> OTHER INFORMATION: Nle, norleucine
<220> FEATURE:
<221> NAME/KEY: MISC_FEATURE
<222> LOCATION: (29)..(29)
<223> OTHER INFORMATION: Gap-NH2, 3-guanidino 2-amino propionic acid
      amide

<400> SEQUENCE: 7

Xaa Ala Asp Ala Ile Phe Thr Asn Ser Tyr Xaa Xaa Val Leu Ala Gln
1               5                   10                  15

Leu Ser Ala Xaa Xaa Leu Leu Gln Asp Ile Xaa Asp Xaa
            20                  25

<210> SEQ ID NO 8
<211> LENGTH: 29
<212> TYPE: PRT
<213> ORGANISM: Artificial sequence
<220> FEATURE:
<223> OTHER INFORMATION: Synthesized
<220> FEATURE:
<223> OTHER INFORMATION: Dat, desaminotyrosine, 3-(4'-hydroxyphenyl)
      propionic acid
<220> FEATURE:
<221> NAME/KEY: MISC_FEATURE
<222> LOCATION: (1)..(1)
<223> OTHER INFORMATION: Dat, desaminotyrosine, 3-(4'-hydroxyphenyl)
      propionic acid
<220> FEATURE:
```

-continued

```
<221> NAME/KEY: MISC_FEATURE
<222> LOCATION: (11)..(12)
<223> OTHER INFORMATION: Gap, 3-guanidino 2-amino propionic acid
<220> FEATURE:
<221> NAME/KEY: MISC_FEATURE
<222> LOCATION: (20)..(20)
<223> OTHER INFORMATION: hArg, homoargininie, 6-guanidino 2-amino
      caproic acid
<220> FEATURE:
<221> NAME/KEY: MISC_FEATURE
<222> LOCATION: (21)..(21)
<223> OTHER INFORMATION: Gap, 3-guanidino 2-amino propionic acid
<220> FEATURE:
<221> NAME/KEY: MISC_FEATURE
<222> LOCATION: (27)..(27)
<223> OTHER INFORMATION: Nle, norleucine
<220> FEATURE:
<221> NAME/KEY: MISC_FEATURE
<222> LOCATION: (29)..(29)
<223> OTHER INFORMATION: Gap-NH2, 3-guanidino 2-amino propionic acid
      amide

<400> SEQUENCE: 8

Xaa Ala Asp Ala Ile Phe Thr Asn Ser Tyr Xaa Xaa Val Leu Ala Gln
1               5                   10                  15

Leu Ser Ala Xaa Xaa Leu Leu Gln Asp Ile Xaa Asp Xaa
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (27)..(27)
<223> OTHER INFORMATION: Nle, norleucine

<400> SEQUENCE: 9

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Xaa Ser Arg
            20                  25
```

ANALOGS OF HUMAN GROWTH HORMONE-RELEASING HORMONE, THEIR PREPARATION AND USE

FIELD OF THE INVENTION

The present invention relates to new peptides—analogs of human growth hormone-releasing hormone, a process for the preparation of new peptides, and their therapeutic uses.

BACKGROUND OF THE INVENTION

The release and synthesis of human growth hormone (GH, somatotropin) are under constant control of two mutually antagonistic hypothalamic hormones—growth hormone release inhibiting hormone (GIH, somatostatin) and growth hormone-releasing hormone. A therapy based on administering human growth hormone-releasing hormone (hGH-RH) may be implemented for majority of patients with GH insufficiency. It has been determined that the shortest fragment, still retaining the full biological activity of endogenous hGH-RH which comprises 44 amino acid residues, is its N-terminal analog hGH-RH(1-29)—$NH_2$. The hGH-RH(1-29)—$NH_2$ peptide can be prepared by synthesis; synthetic GH-RH(1-29)—$NH_2$ under the name sermorelin acetate is approved for use in the treatment of short stature in children and is also under investigation for the treatment of neurosecretion disorders, as an adjuvant for gonadotropin-induced ovulation in infertile women, and for the treatment of AIDS-related catabolic disorders.

It has been disclosed, however, that hGH-RH(1-29)—$NH_2$ is relatively non-resistant to enzymatic degradation. The major metabolites observed are characteristic of bond cleavages between $Arg^{11}$-$Lys^{12}$ and $Lys^{12}$-$Val^{13}$, caused by trypsin-like enzymes (L. A. Frohman, T. R. Downs, E. P. Heimer, A. M. Felix *J. Clin. Invest.* 1989, 83, 1533-1540). It has been determined recently that upon degradation with trypsin of an analog of hGH-RH(1-29)-$NH_2$ the hydrolysis of peptide bonds takes place at the carboxylic group site of all basic amino acid residues, including the C-terminal amide bond, while, for an analog differing in that the Orn residues are present instead of Lys, only the bonds neighboring with Arg residues are hydrolyzed (E. Witkowska, A. Orlowska, B. Sagan, M. Smoluch, J. Izdebski *J. Peptide Sci.* 2000, 6 (*Suppl.*), 189; E. Witkowska, A. Orlowska, B. Sagan, M. Smoluch, J. Izdebski *J. Peptide Sci.* 2001, 7, 166-172). This discovery remains in agreement with the exceptionally high in vivo activity of the analogs containing Orn in positions 12 and 21 (J. Izdebski, J. Pinski, J. E. Horwath, G. Halmos, K. Groot, A. V. Schally, *Proc. Natl. Acad. Sci. USA,* 1995, 92, 4872-4876).

Attempts have been made to overcome the problem of hGH-RH(1-29)-$NH_2$ instability, inter alia by replacing Arg at position 29 in the amino acid sequence with Agm (4-guanidylbutylamine) (Bajusz et al., in *Peptides* 1982, Blaha and Melon, Eds.; W. De Gruyter, Berlin-New York, pp. 643-647), or replacing Tyr at position 1 with Dat (desaminotyrosine) and Lys at position 12 with D-Lys, Arg or Orn (International Patent Application Nos. WO 94/11396 and WO 94/11397).

The results of these attempts, however, are unsatisfactory and the need still exists for analogs combining enhanced ability to release growth hormone with increased resistance to enzymatic degradation, which would allow diminished doses of the drug and/or a less frequent administration.

SUMMARY OF INVENTION

It has now been found by the Inventors that the introduction of selected amino acids to the human growth hormone-releasing hormone analog, not only results in analogs of higher biological activity—better growth hormone release ability, but also has a beneficial influence on the peptides' resistance to enzymes. The selected amino acids comprise D-Arg at position 29, and amino acids containing guanidine groups in their side chain, at the positions occupied in the natural peptide by Lys and Arg.

New peptides—growth hormone-releasing hormone analogs according to the invention have the amino acid sequence of the formula (I):

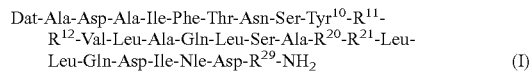

wherein:
$R^{11}$ is hArg, Gab or Gap;
$R^{12}$ is hArg, Orn, Gab or Gap;
$R^{20}$ is hArg, Gab or Gap;
$R^{21}$ is hArg, Orn, Gab or Gap;
$R^{29}$ is D-Arg, hArg, Gab or Gap.

New peptides are potent and selective growth hormone release stimulators and they display a high resistance to enzymatic action.

New peptides or their pharmaceutically acceptable salt may be administered to a patient as such or as the active ingredient of pharmaceutical preparations.

Thus, the present invention also pertains to a pharmaceutical preparation comprising at least one of the new peptides of growth hormone-releasing hormone analogs having the amino acid sequence of the formula (I):

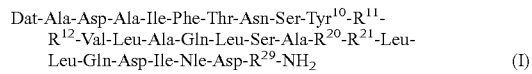

wherein:
$R^{11}$ is hArg, Gab or Gap;
$R^{12}$ is hArg, Orn, Gab or Gap;
$R^{20}$ is hArg, Gab or Gap;
$R^{21}$ is hArg, Orn, Gab or Gap;
$R^{29}$ is D-Arg, hArg, Gab or Gap.

or its pharmaceutically acceptable salt and at least one carrier and/or excipient.

New peptides are useful for the prevention and therapy of disorders associated with the hGH-RH deficiency.

The present invention further provides a method of treating human growth hormone deficiency-related disorders comprising administering to the patient in need of the treatment a therapeutically effective dose of a peptide—hGH-RH analog of formula (I), where $R^{11}$, $R^{12}$, $R^{20}$, $R^{21}$ and $R^{29}$ are as described above.

DETAILED DESCRIPTION OF THE INVENTION

New peptides—growth hormone-releasing hormone analogs have the amino acid sequence of the formula (I):

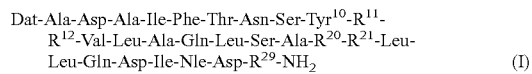

wherein:
$R^{11}$ is hArg, Gab or Gap;
$R^{12}$ is hArg, Orn, Gab or Gap;
$R^{20}$ is hArg, Gab or Gap;
$R^{21}$ is hArg, Orn, Gab or Gap;
$R^{29}$ is D-Arg, hArg, Gab or Gap.

Preferred peptides of this invention comprise:
(1) Dat-Ala-Asp-Ala-Ile-Phe-Thr-Asn-Ser-$Tyr^{10}$-hArg-hArg-Val-Leu-Ala-Gln-Leu-Ser-Ala-$hArg^{20}$-hArg-Leu-Leu-Gln-Asp-Ile-Nle-Asp-$hArg^{29}$-$NH_2$ (SEQ ID NO: 1);

(2) Dat-Ala-Asp-Ala-Ile-Phe-Thr-Asn-Ser-Tyr$^{10}$-hArg-Orn-Val-Leu-Ala-Gln-Leu-Ser-Ala-hArg$^{20}$-Orn-Leu-Leu-Gln-Asp-Ile-Nle-Asp-hArg$^{29}$-NH$_2$ (SEQ ID NO: 2);
(3) Dat-Ala-Asp-Ala-Ile-Phe-Thr-Asn-Ser-Tyr$^{10}$-Gab-Gab-Val-Leu-Ala-Gln-Leu-Ser-Ala-Gab-Gab-Leu-Leu-Gln-Asp-Ile-Nle-Asp-Gab-NH2 (SEQ ID NO: 3);
(4) Dat-Ala-Asp-Ala-Ile-Phe-Thr-Asn-Ser-Tyr$^{10}$-hArg-Gab-Val-Leu-Ala-Gln-Leu-Ser-Ala-Gab-Gab-Leu-Leu-Gln-Asp-Ile-Nle-Asp-Gab-NH$_2$ (SEQ ID NO: 4);
(5) Dat-Ala-Asp-Ala-Ile-Phe-Thr-Asn-Ser-Tyr$^{10}$-Gab-hArg-Val-Leu-Ala-Gln-Leu-Ser-Ala-hArg-hArg-Leu-Leu-Gln-Asp-Ile-Nle-Asp-D-Arg-NH$_2$ (SEQ ID NO: 5);
(6) Dat-Ala-Asp-Ala-Ile-Phe-Thr-Asn-Ser-Tyr$^{10}$-hArg-Gab-Val-Leu-Ala-Gln-Leu-Ser-Ala-hArg-hArg-Leu-Leu-Gln-Asp-Ile-Nle-Asp-D-Arg-NH$_2$ (SEQ ID NO: 6);
(7) Dat-Ala-Asp-Ala-Ile-Phe-Thr-Asn-Ser-Tyr$^{10}$-Gap-Gap-Val-Leu-Ala-Gln-Leu-Ser-Ala-Gap-Gap-Leu-Leu-Gln-Asp-Ile-Nle-Asp-Gap-NH$_2$ (SEQ ID NO: 7);
(8) Dat-Ala-Asp-Ala-Ile-Phe-Thr-Asn-Ser-Tyr$^{10}$-Gap-Gap-Val-Leu-Ala-Gln-Leu-Ser-Ala-hArg-Gap-Leu-Leu-Gln-Asp-Ile-Nle-Asp-Gap-NH$_2$ (SEQ ID NO: 8).

The peptides particularly preferred with regard to biological activity and the resistance to the action of digestive enzymes are:

Dat-Ala-Asp-Ala-Ile-Phe-Thr-Asn-Ser-Tyr$^{10}$-hArg-hArg-Val-Leu-Ala-Gln-Leu-Ser-Ala-hArg$^{20}$-hArg-Leu-Leu-Gln-Asp-Ile-Nle-Asp-hArg$^{29}$-NH$_2$, and Dat-Ala-Asp-Ala-Ile-Phe-Thr-Asn-Ser-Tyr$^{10}$-hArg-Orn-Val-Leu-Ala-Gln-Leu-Ser-Ala-hArg$^{20}$-Orn-Leu-Leu-Gln-Asp-Ile-Nle-Asp-hArg$^{29}$-NH$_2$.

New peptides are useful for the prevention and therapy of disorders associated with the action of human growth hormone-releasing hormone, and therefore they may be used for the treatment of child short stature, old age-related disorders, for the increase of lean body mass and bone mineral content, in wound healing, for treating skin burns and fractured bones, as a nonsteroidal anabolic in chronic ailments-related weakness, and also in diagnostics.

According to the method of the present invention, in the treatment of disorders associated with the action of human growth hormone-releasing hormone a therapeutically effective amount of the peptide—analog of hGH-RH having the amino acid sequence of formula (I) is administered to the patient in need of such therapy.

The dosage level and regimen depend on the particular disease, patient age, weight and condition, and may be determined by a specialist, based on known therapeutic and prophylactic methods for the treatment of human growth hormone-releasing hormone deficiency. In the treatment of diseases of this kind, a suitable dosage unit of a hGH-RH analog is typically from 0.01 to 2 µg per kilogram body weight per dosage. The suitable daily dose may be administered to the patient in one, or a few dosage units per day, with the exception of controlled release forms such as depot forms or implants. Controlled release forms are administered once every 15 days or 30 days, or once every three months.

The peptides of the present invention are usually administered to the patient in any suitable pharmaceutical form, by any acceptable route, such as intravenous, subcutaneous, intramuscular, oral, intranasal or pulmonary inhalation.

New peptides may be administered alone or, optionally, in combination with other therapeutic agents used in the treatment of disorders associated with human growth hormone-releasing hormone deficiency, provided that they do not negatively interfere with each others action. Such compounds may be administered simultaneously as one preparation or in separate preparations, or one after another, in an order and in intervals determined by a specialist. A medical professional will know which drugs and combinations to choose.

The pharmaceutical agents of the present invention comprise at least one active substance, which is a peptide—hGH-RH analog having the amino acid sequence of formula I, or its pharmaceutically acceptable salt, and at least one carrier and/or excipient.

The pharmaceutical preparations of the present invention may be prepared in various pharmaceutical forms, well known to those skilled in the art, such as for example from Remmington's Pharmaceutical Sciences, 18$^{th}$ Ed., Mack Publishing Company, 1990.

Pharmaceutical preparations suitable for injections and infusions include sterile aqueous, aqueous-organic and non-aqueous solutions, suspensions, dry substances and tablets for solution preparation, and implants. The carriers are used for suspension preparation to ensure an even distribution of the active ingredient in the liquid phase and they include polysorbates, lecitine, PEG-polypropylene glycol co-polymers, peptizing agents, such as phosphoranes, polyphosphoranes and citrates of water-soluble polymers such as carboxymethyl cellulose, methyl cellulose, polyvinyl pyrrolidone, gums or gelatin. Preparations for injection may contain pharmaceutically acceptable carriers or excipients, such as pH regulators, buffers, tonics and preservatives. Dry substances are used for the preparation of solutions or extempore suspensions, by dilution with a suitable solvent.

For patient's convenience and in order to achieve appropriate characteristics of substance release, peptide derivatives are conveniently administered as controlled release, prolonged action injection preparations, such as crystalline polymeric microcapsules, comprising the active substance. Another example of time release preparation is a polymer-based implant formulated by dissolution of a biodegradable polymer and the peptides of this invention in a water miscible solvent to form a liquid composition. When injected, the polymer forms a depot, from which the active substance is slowly released.

Pharmaceutical forms suitable for administration by the oral route include tablets, pills, powders, granules, pellets or capsules containing pharmaceutically acceptable solid carriers such as corn starch, lactose, sucrose, sorbitol, hydrous magnesium silicate, stearic acid, magnesium stearate, dicalcium phosphate, or gums. Tablets or granules may be coated or otherwise processed in order to achieve a dosage unit ensuring a preferable time release. For the formation of such protective layers or coatings a number of various substances may be used, comprising polymeric acids and mixtures of polymeric acids with other substances, such as shellac, cetyl alcohol or cellulose acetate.

The pharmaceutical preparation, comprising a peptide as the active substance, may also occur in forms suitable for administration as aerosols or powders for inhalation. A typical aerosol preparation, besides an aqueous solution of the active substance, may contain buffers, isotonic substances, preservatives and, optionally, other excipients enabling administration of the active substance with the help of a dosing sprayer or a dropper.

New peptides of the present invention may be prepared by one of the known chemical synthetic methods, such as classical solution synthesis or solid phase synthesis.

In the solution synthesis method, suitably protected terminal Nα-amino derivatives of amino acids with protected side chains (if reactive side chains are present) or peptide fragments are condensed with appropriately protected carboxylic derivatives of amino acids or peptide fragments. The α-amino function generally is protected in the urethane form, such as the acid-labile tert-butoxycarbonyl group (Boc), benzyloxycarbonyl group (Z, CBz) or they substituted analogs, or in the form of a 9-fluorenylmethoxycarbonyl (Fmoc) protective group, which is labile under basic conditions. Carboxylic functions may be protected as an ester, for example a methyl ester which is unstable in the presence of nucleophilic bases, a tert-butyl ester, which is unstable under acidic conditions or a benzyl ester which is unstable under hydrogenolytic conditions. Carboxyl groups in a protected structure are activated by the azide method, the mixed anhydride method, the activated ester method, the phosphonium or uronium salt methods or by the carbodiimide method, using compounds which catalyze the reaction without causing racemization, such as N-hydroxysuccinimide, 1-hydroxybenzotriazole, 1-hydroxy-7-azabenzotriazole or 3-hydroxy-4-oxo-3,4-dihydro-1,2,3-benzotriazine. The methods of condensation, and the protective groups commonly used in peptide chemistry have been reviewed in *Peptides: Analysis, Synthesis*, Biology, Vol. 3, E. Gross, J. Meienhofer, Eds. (Academic Press, New York, 1981) and *Protective Groups in Organic Synthesis*, Second Edition (Wiley, New York, 1991).

In the solid phase peptide synthesis (SPPS) method proposed by Merrifield (*J. Am. Chem. Soc.* 85 (1963), 2149) an insoluble in the reaction medium polymer support, containing a functional group, to which the first amino acid may be attached, is used. The polymer matrix serves as permanent C-terminal protecting group. Synthesis starts with attachment of the first Na-protected amino acid to the linker functionality. After deprotection of the amino function another activated protected amino acid is added. Chain elongation is accomplished by consecutive deprotection and coupling steps. Finally, the N-terminal free peptide is cleaved from the resin, with concomitant deprotection of side chain functional groups. The insoluble support is easily filtered from the peptide solution. Polymers suitable as support phases are e.g. cellulose, polyvinyl alcohol, polymethacrylates, chloromethylated divinylbenzene-polystyrene copolymer, 4-methylbenzhydrylamine resin (MBHA resin), benzhydrylamine resin (BHA) and the like. The synthesis of peptides on polymer support is carried out in solvents, which dissolve the amino acid derivatives used and are neutral under the reaction conditions. Preferred are solvents, which additionally have good swelling properties, such as dimethylformamide, dichloromethane, N-methyl-2-pyrrolidone, acetonitrile, dimethyl sulfoxide, and their mixtures. After the amino acid has been cleaved from the polymer support, it is purified, for example using high performance liquid chromatography.

New peptides—GH-RH analogs of the present invention, comprising a guanidine group in the amino acids' side chains, are preferably prepared using the solid phase synthesis method, by introducing suitable derivatives of lysine, 2,4-diaminobutyric acid or 2,3-diaminopropionic acid at appropriate positions in the peptide chain attached to a polymeric support, deprotecting side-chain amino groups and reacting free amino groups with a guanidinating agent, removing all remaining t-butyloxycarbonyl protective groups, and cleaving the synthesized peptide from the support, followed by purification and, optionally, converting the peptide into a pharmaceutically acceptable salt.

The guanidination reaction is carried out using an excess of a guanidinylating agent, such as N,N'-bis(tert-butyloxycarbonyl)-S-methylisothiourea, in the presence of a reaction promoter, such as 4-(dimethylamino)pyridine.

The peptides synthesized are purified, preferably by the high performance liquid chromatography method, in order to achieve a high degree of purity suitable for pharmaceutical uses.

New peptides may be isolated from the reaction mixture in the form of pharmaceutically acceptable salts of various inorganic and organic acids and bases. New peptides may form pharmaceutically acceptable salts with inorganic acids, such as: hydrochloric acid, hydrobromic acid, sulfuric acid, nitric acid, phosphoric acid, or with organic acids, such as: acetic, propionic, maleic, fumaric, malonic, succinic, tartaric, citric, ascorbic, malic, oxalic, cinnamic, mandelic, benzoic, methanesulfonic, ethanesulfonic, p-toluenesulfonic acid, and other acids.

The salts may be prepared also by reacting the carboxylic grouping of the peptide with alkali metals, hydroxides and alkanoates of alkali metals, as well as with organic bases, such as trimethylamine, diethylamine, ethanolamine, piperidine, choline, and the like.

The salts may be prepared by known methods, by reacting a substance in the form of a free base or acid with one or more equivalent of a suitable base or acid, respectively, in a solvent or in a medium, in which the salt is insoluble.

Acetic acid salts of new peptides—analogues of hGH-RH are a preferred embodiment of the present invention.

Biological Activity Determination

In order to test the biological activity of new peptides of the present invention, their influence on the plasma level of growth hormone and other pituitary hormones in rats was investigated and compared with the influence of hGH-RH(1-29)$NH_2$ as the reference substance.

The investigated materials were: hGH-RH(1-29)$NH_2$ purchased from Sigma Chemical Co., and peptides—analogs of hGH-RH synthesized by the process of the present invention.

Male Wistar rats (240-260 g) were housed under controlled light schedule of 14-h light, 10-h dark and provided with rat pellets and waters ad libitum. The animals were randomly assigned into experimental groups, which received saline (0.9% NaCl; 0.3 ml), hGH-RH(1-29)$NH_2$ in a dose of 50 or 150 µg/kg of body weight, and peptides of the present invention in a dose of 1 or 3 µg/kg of body weight. The rats received a single subcutaneous (sc.) injection of the reference peptide or each of the new analogs tested, dissolved in 0.3 ml saline.

On the day of the experiment, rats were anaesthetized with an intraperitoneal injection of ketamine (120 mg/kg) and the jugular vein was chronically cannulated for blood collection. Thirty minutes later, the tested substances were sc. injected. The control group of rats was injected only with saline. Blood (approximately 0.6 ml) was taken from the jugular vein 1-minute (sample "0") before, and 15- and 30-minutes after the tested substance was sc. administered. An equivalent volume of heparinized saline (10 UI/ml) was replaced at each sample removal. At the end of the experiment, the animals were put to death with an anaesthetic overdose of ketamine. The blood samples were centrifuged, and the plasma samples (approximately 0.3 ml) were separated and stored at −20° C., until assayed by RIA methods.

Plasma concentrations of the growth hormone, prolactin, luteinizing hormone, follicle stimulating hormone, and thyrotropin (GH, PRL, LH, FSH and TSH) were determined for 0.05 ml aliquots of the plasma samples, using kits provided by Biotrak (Amersham Life Science, England). The sensitivity for rat GH, PRL, LH, FSH and TSH was 0.16, 0.08, 0.08, 0.09 and 0.05 ng/tube, respectively.

The statistical analysis of results was performed using Statsoft Statistica PL for Windows. Initially, all groups of data were tested for normality by the Kolmogarov-Smirnow test and Shapir-Wilka test. Statistical differences between the groups were determined by one-way ANOVA. Duncan's multiple range test was used to make post hoc comparisons. However, when variances were found to be significantly heterogeneous, the comparisons between groups were carried out by non-parametric Kruskal-Wallis Analysis of Variance on Ranks.

Individual differences in hormone levels were eliminated via correction of the hormone level, calculating the net concentration of the hormone for each rat. This net concentration for each hormone was calculated as a difference between the concentration 15 minutes after the injection of the compound and the concentration of the hormone before the injection of the compound (Δ15-0), and the difference between the concentration of the hormone 15 minutes, and 30 minutes after the injection of the compound (Δ15-30).

The influence of the compounds on GH release was determined by comparison of the mean net GH concentration (Δ15-0) after the injection of hGH-RH-(1-29)NH$_2$ in doses of 50.0 µg and 150.0 µg per kg of body weight, and of 1.0 µg and 3.0 µg for the analogs, per kg of body weight. The results for a selected compound (1) are presented in Tables 1 and 2. The significant differences between treatment groups were determined by the Lillietor's modification of the Kruskal-Wallis test.

TABLE 1

The effect of subcutaneous administration of hGH-RH peptides and their analogs on GH release in male rats.

| Compound | Dose [µg/kg] | Number of rats | Plasma GH at various times after injection [ng/kg] | | |
|---|---|---|---|---|---|
| | | | 0 min. | 15 min. | 30 min. |
| Saline | 50 | 11 | 21.4 ± 2.9 | 19.8 ± 3.9 | 17.8 ± 2.7 |
| hGH-RH(1-29)-NH$_2$ | 50 | 11 | 24.5 ± 2.7 | 79.1 ± 7.9* | 39.0 ± 5.9* |
| | 150 | 11 | 27.1 ± 3.2 | 163 ± 18** | 103 ± 15** |
| Compound 1 | 1 | 9 | 23.1 ± 2.0 | 99.1 ± 16** | 42.5 ± 9.2* |
| | 3 | 9 | 28.3 ± 4.1 | 130 ± 16** | 58.4 ± 8.9** |

The results are expressed as mean ± SEM
*P < 0.01 vs. saline control
**P < 0.001 vs. saline control

TABLE 2

Changes in GH concentration after subcutaneous administration of hGH-RH analogs

| Compound | Dose [µg/kg] | Number of rats | Net GH concentration at various times after injection [ng/ml] | |
|---|---|---|---|---|
| | | | Δ(15 − 0)# | Δ(15 − 30)# |
| Saline | 50 | 11 | −1.59 ± 1.5 | 1.97 ± 1.5 |
| hGH-RH(1-29)-NH$_2$ | 50 | 11 | 54.6 ± 7.9** | 40.1 ± 6.7** |
| | 150 | 11 | 135 ± 16.9** | 59.9 ± 16.6** |
| Compound 1 | 1 | 9 | 75.9 ± 16.0** | 56.5 ± 14.7** |
| | 3 | 9 | 102 ± 12.6** | 72.0 ± 12.6** |

The results are expressed as mean DGH [ng/ml].
Changes of the plasma GH (ΔGH) were expressed as a net GH concentration and were calculated for each rat.
Δ(15 − 0) was calculated as a difference between GH concentration at 15 min. after administration of the tested compound and GH concentration before injection of the compound ("0 min"). Δ(15 − 30) was calculated as a difference between GH concentration at 15 min. after administration of the tested compound and GH concentration at 30 min. after the injection of the compound.
**P < 0.001 vs. saline control The results obtained indicate that the tested hGH-RH analogs display a stimulating effect on GH release in rats, compared with saline control. The strongest stimulating effect was displayed by the compound designated as (1). The maximum stimulating effect was observed after 15 minutes from the moment of their administration. This effect was observed as long as 30 minutes after administration. The influence of compound 1 on the net GH concentration was comparable with the net concentration of this hormone at 15 minutes after the injection of hGH-RH-(1-29)—NH$_2$ in a dose 50 times higher. The relative potency of compound 1 was based on doses 1.0 and 3.0 µg, and on the doses of 50 and 150 µg of hGH-RH-(1-29)—NH$_2$ per kg of body weight. The relative potency of this new analog was 70 and 38 times higher, respectively, compared with hGH-RH-(1-29)—NH$_2$ at 15 minutes after the injection.

In the course of this investigation it has also been determined that new compounds of the present invention act selectively and they do not have any influence on the blood concentration levels of other pituitary hormones—prolactin, lutropin, follitropin and thyreotropin, in the peripheral blood of rats.

The compounds prepared were also tested for enzymatic resistance in the trypsin digestion test.

A peptide sample (1.2 mg) was dissolved in a pH 8.5 buffer (2.9 ml; 0.05 M ammonium acetate solution) and incubated at 37° C. for 20 minutes. Subsequently, a trypsin solution was added (100 µl; 0.02 mg/ml; Serva, 36 U/mg). The resulting solution was incubated at 37° C. for 60 minutes. An aliquot (500 µl) was withdrawn and diluted with 0.5 M acetic acid (1 ml), then lyophilized. The material obtained was analyzed by HPLC, using a Knauer system with an Eurospher 100 C18 (4.6×250 mm, 5 micron) column. The following solvent systems were used: A, 0.1% TFA in water; B, 80% solution of acetonitrile in A; with a linear gradient of 25-70% B; flow rate of 1 ml/minute; detection was carried out at 220 nanometers. The results of peptide digestion are summarized in Table 3.

TABLE 3

Trypsin digestion of RH-GH analogs

| Compound No. | Digestion time [min.] | % Unchanged compound |
|---|---|---|
| 1 | 30 | >99 |
| | 60 | >99 |
| 2 | 30 | >99 |
| | 60 | >99 |
| 3 | 30 | 86 |
| | 60 | 72 |
| 4 | 30 | 82 |
| | 60 | 67 |
| 5 | 30 | 80 |
| | 60 | 51 |
| 6 | 30 | 85 |
| | 60 | 73 |
| 7 | 30 | 75 |
| | 60 | 68 |
| 8 | 30 | >99 |
| | 60 | >99 |
| Reference* | 30 | 0 |
| | 60 | 0 |

*Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$(hGH-RH(1-29)—NH$_2$)

The results presented in Table 3 indicate that all the new analogs of hGH-RH tested have a much higher resistance to trypsin digestion than the reference standard, hGH-RH(1-29)—NH$_2$. Thus, after 30 minutes, under the conditions resulting in a complete digestion of the reference peptide, other peptides remain either unchanged [peptide (1), (2) and (8)] or they undergo only a limited hydrolysis.

New peptides of the present invention are characterized by a high growth hormone-release activity, they act selectively and do not influence the level of other pituitary hormones—prolactin, lutropin, follitropin and thyreotropin. The particularly preferred peptide has the amino acid sequence Dat-Ala-Asp-Ala-Ile-Phe-Thr-Asn-Ser-Tyr-hArg-hArg-Val-Leu-Ala-Gln-Leu-Ser-Ala-hArg-hArg-Leu-Leu-Gln-Asp-Ile-Nle-Asp-hArg-NH$_2$ (SEQ ID NO: 1), and displays a many times stronger effect on growth hormone release than the reference peptide hGH-RH(1-29)NH$_2$, thus allowing for a maximum stimulating effect after 15 minutes. Simultaneously, the new compounds of this invention exhibit a much higher resistance to the action of digestive enzymes than the known synthetic analogs of hGH-RH do, which makes the new compounds particularly useful for applications in the preparation of pharmaceutical agents used in the therapy and prevention of growth hormone insufficiency-related disorders.

DEFINITIONS AND CONVENTIONS

The definitions and explanations below are for the terms as used throughout this entire document including both the specifications and the claims.

DEFINITIONS

The amino acid nomenclature and abbreviations have been used herein in accordance with the generally accepted IUPAC-IUB rules e.g. R. M. Schultz, M. N. Liebman *Proteins: Composition and Structure*, Chapter 2, in: *Textbook of Biochemistry*, 3$^{rd}$ Edition, T. M. Devlin, Ed.; Wiley-Liss, New York, 1992; and *European J. Biochem.* 138 (1984), 9-37. The three-letter abbreviations used herein have the following meaning:

| | |
|---|---|
| Ala | alanine |
| Arg | arginine |
| hArg | homoarginine (6-guanidine-2-caproic acid) |
| Asn | asparagine |
| Asp | aspartic acid |
| Dat | desaminotyrosine, 3-(4'-hydroxyphenyl)propionic acid |
| Gln | glutamine |
| Gab | 4-guanidine-2-aminobutyric acid |
| Gap | 3-guanidine-2-aminopropionic acid |
| Ile | isoleucine |
| Leu | leucine |
| Lys | lysine |
| Nle | norleucine |
| Orn | ornithine |
| Phe | phenylalanine |
| Ser | serine |
| Thr | threonine |
| Tyr | tyrosine |
| Val | valine |

All the peptide sequences cited in the preceding description, in the examples and in the appended claims have been written in a standard convention under which the N-terminal amino acid begins, and the C-terminal amino acid ends the sequence. The amino acids are in the L configuration, unless stated otherwise.

The present invention will now be described with reference to the following specific, non-limiting examples.

EXAMPLES

General Methodology for Peptide Synthesis

A. Peptide Chain Formation

To protect the α-amino functional groups the t-butyloxycarbonyl (Boc) group was used; the side chains were protected with the following groups: Asp—with cyclohexyl; Orn—benzyloxycarbonyl; Ser and Thr—benzyl; Tyr—2-bromobenzyloxycarbonyl group.

In order to prepare the analogs containing the hArg residue, lysine residues in the form of the Boc-Lys(Fmoc) derivative were introduced at appropriate positions in the peptide chain.

In order to prepare the analogs containing the Gab and/or Gap residues, 2,4-diaminobutyric acid residues and 2,3-diaminopropionic acid residues were introduced at appropriate positions, in the form of Boc-Dab(Fmoc) and Boc-Dap(Fmoc) derivatives, respectively.

In order to prepare the analogs containing the Orn residue, the Boc-Orn(Z) derivative was introduced during the synthesis at appropriate positions in the peptide chain.

The MBHA resin (4-methylbenzhydrylamine resin, Bachem California or Novabiochem, ca. 0.5 meq./g), after swelling in dichloromethane (DCM) for 30 minutes, was treated with a 5% diisopropylethylamine (DIEA) solution in DCM (1×1 min., 1×20 min.) and washed with DCM (6×1 min.).

The protected peptidyl resins were synthesized using standard procedures in each synthetic step, according to the following protocol:

(a) Removal of the Boc group with a 55% trifluoroacetic acid (TFA) solution in DCM (1×1 min., 1×20 min.);
(b) DCM wash (3×1 min.);
(c) Washing with a 30% 1,4-dioxane/DCM solution (2×1 min.);
(d) DCM wash (3×1 min.);
(e) Neutralizing with 5% DIEA/DCM (1×1 min., 1×5 min.);
(f) DCM wash (6×1 min.);
(g) Coupling of the Boc-amino acid (1.2 mmol) by the carbodiimide method, using N,N'-diisopropylcarbodiimide (DIC), 1.2 mmol, in DCM, reaction time: 2 hours. In the case of Boc-Gln and Boc-Asn, N-hydroxybenzotriazole (HOBt), 1.2 mol, was added to the reaction mixture;
(h) DCM wash (6×1 min.).

B. Introduction of Guanidine Groups

In order to remove the Fmoc group from the Lys residue, the protected peptidyl resin was subjected to a 50% piperidine/DMF solution (1×10 min., 1×2 h), then the resin was washed with dimethylformamide (DMF) (3×1 min.), with a 50% DMF/DCM solution (3×2 min.), a 50% methanol/DCM solution, and with DCM (3×2 min.). The peptidyl resin was then reacted with N,N'-bis(tert-butyloxycarbonyl)-S-methyl-isothiourea (five-fold molar excess) in the presence of 4-(dimethylamino)pyridine (70 mg) in DMF, for 4 days. The peptidyl resin obtained was washed with DMF (3×1 min.), and with DCM (3×1 min.), the Boc groups were removed with a 55% TFA/DCM solution (1×1 min., 1×20 min., 1×40 min.), followed by a DCM wash (3×1 min.), a 50% DMF/DCM wash (2×1 min.) and a DCM wash (2×1 min.).

C. Cleavage of the Peptide from the Resin

The peptidyl resin was subjected to liquid hydrogen fluoride (HF), in the presence of anisole. The reaction was carried out for 1 hour at 0° C. Afterwards, the HF was removed under reduced pressure, the residue was washed with cold diethyl ether and extracted with a 50% acetic acid solution, then lyophilized.

D. Peptide Purification

The crude peptides were purified by the high performance liquid chromatography method, using a Knauer system with a Vertex column, Nucleosil-300 C18 (B×200 mm, 5 micron). The following solvent systems were used: A, 0.1% TFA in water solution; B, 80% solution of MeCN in A. The elution was carried out in a gradient mode of 20-55% B for 30 minutes, then isocratic 55% B for 30 minutes, at the flow rate of 2 ml/minute. The fractions were analyzed with a Vertex column, Nucleosil 100 C18 (4×250 mm, 5 micron), run in a gradient mode 25-70% for 30 min.; flow rate: 1 ml/min. The detection was performed at 220 nm. The homogeneous fractions (single peak on chromatograms) were pooled, diluted with water and lyophilized to give a chromatographically homogeneous product. The structures of peptides were determined with ESI-MS mass spectra run on a Finnigan MAT 95S (Bremen, Germany) spectrometer.

Example 1

Preparation of Dat-Ala-Asp-Ala-Ile-Phe-thr-Asn-Ser-Tyr-hArg-hArg-Val-Leu-Ala-Gln-Leu-Ser-Ala-hArg-Leu-Leu-Gln-Asp-Ile-Nle-Asp-hArg-$NH_2$ (SEQ ID NO: 1) [compound (I)]

3.1 g of MBHA resin (4-methylbenzhydrylamine resin, Novabiochem, 0.49 meq./g), after the attachment of suitably protected amino acid derivatives according to the foregoing general methodology of peptide synthesis (section A), afforded the fully protected peptidyl resin: Dat-Ala-Asp (OcHex)-Ala-Ile-Phe-Thr(OBzl)-Asn-Ser(OBzl)-Tyr(2-Br—Z)-Lys (Fmoc)-Lys (Fmoc)-Val-Leu-Ala-Gln-Leu-Ser-Ala-Lys (Fmoc)—Lys (Fmoc)-Leu-Leu-Gln-Asp (OcHex)-Ile-Nle-Asp (OcHex)-Lys(Fmoc)-resin.

A subsequent procedure, according to the foregoing general methodology of peptide synthesis (section B), after removal of all Fmoc protective groups and an exhaustive guanidination, followed by all Boc groups deprotection, afforded 9.53 g of the peptidyl resin Dat-Ala-Asp-Ala-Ile-Phe-Thr-Asn-Ser-Tyr-hArg-hArg-Val-Leu-Ala-Gln-Leu-Ser-Ala-hArg-hArg-Leu-Leu-Gln-Asp-Ile-Nle-Asp-hArg-$NH_2$-resin (SEQ ID: NO: 1).

This resin was subjected to the action of liquid hydrogen fluoride (200 ml HF), in the presence of anisole (15 ml), according to the foregoing general methodology of peptide synthesis (section C), which furnished 4.5 g of the crude peptide of 50% purity, based on HPLC determination.

The crude peptide (a 20 mg sample) was purified by the high performance liquid chromatography method, according to the general methodology of synthesis (section D above). This afforded 4.3 mg of the title peptide of 92.3% purity (based on HPLC); mass spectrum: for $C_{157}H_{258}N_{47}O_{43}$, M=3492.0; registered m/z:

[M+2H]$^{2+}$: calculated 1747.0, found 1747.6;
[M+3H]$^{3+}$: calculated 1165.0, found 1165.4;
[M+4H]$^{4+}$: calculated 874.0, found 874.0;
[M+5H]$^{5+}$: calculated 699.4, found 699.4.

Example 2

Preparation of Compounds (2)-(8)

Using suitably protected amino acids in a procedure fully analogous with the foregoing specific description, the following peptides were synthesized:

(2) Dat-Ala-Asp-Ala-Ile-Phe-Thr-Asn-Ser-Tyr[10]-hArg-Orn-Val-Leu-Ala-Gln-Leu-Ser-Ala-hArg[20]-Orn-Leu-Leu-Gln-Asp-Ile-Nle-Asp-hArg[29]-$NH_2$ (SEQ ID NO: 2); MS: for $C_{153}H_{251}N_{43}O_{43}$, M=3380.9; registered m/z:
[M+3H]$^{3+}$: calculated 1128.0, found 1127.9;
[M+4H]4$^+$: calculated 846.2, found 846.2;
[M+H]5$^+$: calculated 677.2, found 676.9.

(3) Dat-Ala-Asp-Ala-Ile-Phe-Thr-Asn-Ser-Tyr[10]-Gab-Gab-Val-Leu-Ala-Gln-Leu-Ser-Ala-Gab-Gab-Leu-Leu-Gln-Asp-Ile-Nle-Asp-Gab-NH2 (SEQ ID NO: 3); MS: for $C_{147}H_{238}N_{47}O_{43}$, M=3351.8, registered m/z:
/[M+3H]$^{3+}$: calculated 1118.3, found 1118.6;
[M+4H]4$^+$: calculated 839.0 found 839.2;
[M+5H]5$^+$: calculated 671.4, found 671.6.

(4) Dat-Ala-Asp-Ala-Ile-Phe-Thr-Asn-Ser-Tyr[10]-hArg-Gab-Val-Leu-Ala-Gln-Leu-Ser-Ala-Gab-Gab-Leu-Leu-Gln-Asp-Ile-Nle-Asp-Gab-$NH_2$ (SEQ ID NO: 4); MS: for $C_{149}H_{242}N_{47}O_{43}$, M=3379.8; registered m/z:
[M+4H]$^{4+}$: calculated 846.0 found 846.3;
[M+5H]$^{5+}$: calculated 677.0, found 677.2.

(5) Dat-Ala-Asp-Ala-Ile-Phe-Thr-Asn-Ser-Tyr[10]-Gab-hArg-Val-Leu-Ala-Gln-Leu-Ser-Ala-hArg-hArg-Leu-Leu-Gln-Asp-Ile-Nle-Asp-D-Arg-$NH_2$(SEQ ID NO: 5); MS: for $C_{154}H_{253}N_{47}O_{43}$, M=3451.0; registered m/z:
[M+3H]$^{3+}$: calculated 1151.3, found 1152.0;
[M+4H]4$^+$: calculated 863.8, found 863.8
[M+H]5$^+$: calculated 691.2, found 691.6.

(6) Dat-Ala-Asp-Ala-Ile-Phe-Thr-Asn-Ser-Tyr[10]-hArg-Gab-Val-Leu-Ala-Gln-Leu-Ser-Ala-hArg-hArg-Leu-Leu-Gln-Asp-Ile-Nle-Asp-D-Arg-$NH_2$ (SEQ ID NO: 6); MS: for $C_{154}H_{253}N_{47}O_{43}$, M=3451.0; registered m/z:
[M+3H]$^{3+}$: calculated 1151.3, found 1151.4;
[M+4H]4$^+$: calculated 863.8, found 863.6;
[M+H]5$^+$: calculated 691.2, found 691.3.

(7) Dat-Ala-Asp-Ala-Ile-Phe-Thr-Asn-Ser-Tyr[10]-Gap-Gap-Val-Leu-Ala-Gln-Leu-Ser-Ala-Gap-Gap-Leu-Leu-Gln-Asp-Ile-Nle-Asp-Gap-$NH_2$ (SEQ ID NO: 7); MS: for $C_{142}H_{229}N_{47}O_{43}$, M=3282.7; registered m/z:
[M+3H]$^{3+}$: calculated 1095.2, found 1095.3;
[M+4H]4$^+$: calculated 821.7, found 821.7;
[M+H]5$^+$: calculated 657.5, found 657.8.

(8) Dat-Ala-Asp-Ala-Ile-Phe-Thr-Asn-Ser-Tyr[10]-Gap-Gap-Val-Leu-Ala-Gln-Leu-Ser-Ala-hArg-Gap-Leu-Leu-Gln-Asp-Ile-Nle-Asp-Gap-$NH_2$ (SEQ ID NO: 8) MS: for $C_{145}H_{235}N_{47}O_{43}$, M=3324.8; registered m/z:
[M+3H]$^{3+}$: calculated 1109.3 found 1109.6;
[M+4H]4$^+$: calculated 832.2, found 832.2;
[M+H]5$^+$: calculated 666.0, found 666.0.

The invention claimed is:

1. A growth hormone-releasing hormone analog having the amino acid sequence of the formula (I):

Dat-Ala-Asp-Ala-Ile-Phe-Thr-Asn-Ser-Tyr$^{10}$-R$^{11}$-
R$^{12}$-Val-Leu-Ala-Gln-Leu-Ser-Ala-R$^{20}$-R$^{21}$-Leu-
Leu-Gln-Asp-Ile-Nle-Asp-R$^{29}$-NH$_2$ (I)

wherein:
R$^{11}$ is hArg, Gab or Gap;
R$^{12}$ is hArg, Gab or Gap;
R$^{20}$ is hArg, Gab or Gap;
R$^{21}$ is hArg, Gab or Gap;
R$^{29}$ is D-Arg, hArg, Gab or Gap;
wherein hArg is 6-guanidino-2-caproic acid, Gab is 4-guanidine-2-aminobutyric acid and Gap is 3-guanidine-2-aminopropionic acid;
or a pharmaceutically acceptable salt thereof.

2. A peptide according to claim 1 selected from the group consisting of:

Dat-Ala-Asp-Ala-Ile-Phe-Thr-Asn-Ser-Tyr$^{10}$-hArg-hArg-Val-Leu-Ala-Gln-Leu-Ser-Ala-hArg$^{20}$-hArg-Leu-Leu-Gln-Asp-Ile-Nle-Asp-hArg$^{29}$-NH$_2$ (SEQ ID NO: 1);

(2) Dat-Ala-Asp-Ala-Ile-Phe-Thr-Asn-Ser-Tyr$^{10}$-Gab-Gab-Val-Leu-Ala-Gln-Leu-Ser-Ala-Gab-Gab-Leu-Leu-Gln-Asp-Ile-Nle-Asp-Gab-NH2 (SEQ ID NO: 3);

(3) Dat-Ala-Asp-Ala-Ile-Phe-Thr-Asn-Ser-Tyr$^{10}$-hArg-Gab-Val-Leu-Ala-Gln-Leu-Ser-Ala-Gab-Gab-Leu-Leu-Gln-Asp-Ile-Nle-Asp-Gab-NH$_2$ (SEQ ID NO: 4);

(4) Dat-Ala-Asp-Ala-Ile-Phe-Thr-Asn-Ser-Tyr$^{10}$-Gab-hArg-Val-Leu-Ala-Gln-Leu-Ser-Ala-hArg-hArg-Leu-Leu-Gln-Asp-Ile-Nle-Asp-D-Arg-NH$_2$ (SEQ ID NO: 5);

(5) Dat-Ala-Asp-Ala-Ile-Phe-Thr-Asn-Ser-Tyr$^{10}$-hArg-Gab-Val-Leu-Ala-Gln-Leu-Ser-Ala-hArg-hArg-Leu-Leu-Gln-Asp-Ile-Nle-Asp-D-Arg-NH$_2$ (SEQ ID NO: 6);

(6) Dat-Ala-Asp-Ala-Ile-Phe-Thr-Asn-Ser-Tyr$^{10}$-Gap-Gap-Val-Leu-Ala-Gln-Leu-Ser-Ala-Gap-Gap-Leu-Leu-Gln-Asp-Ile-Nle-Asp-Gap-NH$_2$ (SEQ ID NO: 7); and (7) Dat-Ala-Asp-Ala-Ile-Phe-Thr-Asn-Ser-Tyr$^{10}$-Gap-Gap-Val-Leu-Ala-Gln-Leu-Ser-Ala-hArg-Gap-Leu-Leu-Gln-Asp-Ile-Nle-Asp-Gap-NH$_2$ (SEQ ID NO: 8).

3. The peptide of claim 2 which is
Dat-Ala-Asp-Ala-Ile-Phe-Thr-Asn-Ser-Tyr$^{10}$-hArg-hArg-Val-Leu-Ala-Gln-Leu-Ser-Ala-hArg$^{20}$-hArg-Leu-Leu-Gln-Asp-Ile-Nle-Asp-hArg$^{29}$-NH$_2$ (SEQ ID NO: 1).

4. A process for the preparation of growth hormone-releasing hormone analogs having the amino acid sequence of the formula (I):

Dat-Ala-Asp-Ala-Ile-Phe-Thr-Asn-Ser-Tyr$^{10}$-R$^{11}$-R$^{12}$-Val-Leu-Ala-Gln-Leu-Ser-Ala-R$^{20}$-R$^{21}$-Leu-Leu-Gln-Asp-Ile-Nle-Asp-R$^{29}$-NH$_2$     (I)

where:
R$^{11}$ is hArg, Gab or Gap;
R$^{12}$ is hArg, Gab or Gap;
R$^{20}$ is hArg, Gab or Gap;
R$^{21}$ is hArg, Gab or Gap;
R$^{29}$ is D-Arg, hArg, Gab or Gap;
wherein hArg is 6-guanidino-2-caproic acid, Gab is 4-guanidine-2-aminobutyric acid and Gap is 3-guanidine-2-aminopropionic acid and their pharmaceutically acceptable salts, using the solid phase synthesis method, comprising introducing suitable derivatives of lysine, 2,4-diaminobutyric acid or 2,3-diaminopropionic acid as a precursor of hArg, Gab and Gap, respectively at one or more of positions 11, 12, 20, 21 and 29 of the peptide chain attached to a polymeric support, deprotecting side-chain amino groups and reacting free amino groups with N,N'-bis(tert-butyloxycarbonyl)-S-methylisothiourea as a guanidinating agent in the presence of 4-(dimethylamino)pyridine, removing all remaining protective groups, and cleaving the synthesized peptide from the support, followed by purification and, optionally, converting the peptide into a pharmaceutically acceptable salt thereof.

5. The process according to claim 4 where 4-methylbenzhydrylamine-resin is used as the polymeric support.

6. The process according to claim 4 where the synthesized peptide is cleaved from the support using hydrogen fluoride.

7. The process according to claim 4 where the synthesized peptide is purified by the high performance liquid chromatography method.

8. A pharmaceutical preparation comprising an active substance, one or more carriers and/or one or more excipients wherein the active substance is at least one of the growth hormone-releasing hormone analogs having the amino acid sequence of the formula (I):

Dat-Ala-Asp-Ala-Ile-Phe-Thr-Asn-Ser-Tyr$^{10}$-R$^{11}$-R$^{12}$-Val-Leu-Ala-Gln-Leu-Ser-Ala-R$^{23}$-R$^{21}$-Leu-Leu-Gln-ASp-Ile-Nle-Asp-R$^{29}$-NH$_2$     (I)

where:
R$^{11}$ is hArg, Gab or Gap;
R$^{12}$ is hArg, Gab or Gap;
R$^{20}$ is hArg, Gab or Gap;
R$^{21}$ is hArg, Gab or Gap;
R$^{29}$ is D-Arg, hArg, Gab or Gap;
wherein hArg is 6-guanidino-2-caproic acid, Gab is 4-guanidine-2-aminobutyric acid and Gap is 3-guanidine-2-aminopropionic acid;
or a pharmaceutically acceptable salt thereof.

9. A method of treating human growth hormone deficiency-related disorders comprising administering to a patient in need a therapeutically effective dose of a peptide hGH-RH analog, having the amino acid sequence of the formula (I)

Dat-Ala-Asp-Ala-Ile-Phe-Thr-Asn-Ser-Tyr$^{10}$-R$^{11}$-R$^{12}$-Val-Leu-Ala-Gln-Leu-Ser-Ala-R$^{20}$-R$^{21}$-Leu-Leu-Gln-Asp-Ile-Nle-Asp-R$^{29}$-NH$_2$     (I)

wherein:
R$^{11}$ is hArg, Gab or Gap;
R$^{12}$ is hArg, Gab or Gap;
R$^{20}$ is hArg, Gab or Gap;
R$^{21}$ is hArg, Gab or Gap;
R$^{29}$ is D-Arg, hArg, Gab or Gap;
wherein hArg is 6-guanidino-2-caproic acid, Gab is 4-guanidine-2-aminobutyric acid and Gap is 3-guanidine-2-aminopropionic acid
or of a pharmaceutically acceptable salt thereof.

* * * * *